United States Patent [19]

Bowen et al.

[11] Patent Number: 5,346,908
[45] Date of Patent: Sep. 13, 1994

[54] NITROGEN-CONTAINING CYCLOHETERO CYCLOHETEROAMINOARYL DERIVATIVES FOR CNS DISORDERS

[75] Inventors: Wayne Bowen, Derwood; Brian R. de Costa, Rockville; Celia Dominguez, Gaithersburg; Xiao-Shu He, Derwood; Kenner C. Rice, Bethesda, all of Md.

[73] Assignees: National Institutes of Health, Bethesda, Md.; Brown University, Providence, R.I.

[21] Appl. No.: 904,354

[22] Filed: Jun. 25, 1992

[51] Int. Cl.$^5$ ............ A61K 31/55; A61K 31/445; A61K 31/40; C07D 211/08
[52] U.S. Cl. ............ 514/316; 514/212; 514/324; 514/326; 514/422; 540/596; 540/597; 540/602; 546/187; 546/191; 546/202; 546/208; 548/518
[58] Field of Search ............ 546/187, 202, 208, 191; 514/316, 324, 326

[56] References Cited

U.S. PATENT DOCUMENTS

| | | | |
|---|---|---|---|
| 4,204,003 | 5/1980 | Szmuszkovicz | 424/324 |
| 4,463,013 | 7/1984 | Collins et al. | 424/274 |
| 4,801,604 | 1/1989 | Vonvoightlander et al. | 514/429 |

OTHER PUBLICATIONS de Costa et al., FEBS Letters, vol. 251, pp. 53–58 (1989).
de Costa et al., J. Med. Chem. 35 (23), 4334–43 (1992).
S. M. Rothman et al., *Annals of Neurology*, vol. 19, No. 2, 105–111 (1986).
C. Carter et al., *J. Pharm. Exp. Ther.*, 247 (3), 1222–1232 (1988).
F. F. Gilman et al., *The Phramacological Basis of Therapeutics*, 7th ed., 404, MacMillan (1985).
C. G. Parsons et al., *Neuropharm.*, 25(2)), 217–220 (1986).
W. Lason et al., *Brain Res.*, 482, 333–339 (1989).
B. R. de Costa et al., *J. Med. Chem.*, 32(8), 1996–2002 (1989).
Long et al., *Soc. Neurosci. Abs.* 16, 1122, abs. 461.4 (1990).
P. C. Contreras et al., *Brain Res.*, 546, 79–82 (1991).
Scopes et al., *J. Med. Chem.*, 35, 490–501 (1992).
B. R. de Costa et al., *J. Med. Chem.*, 35(1), 38–47 (1992).
L. Radesca et al., *J. Med. Chem.*, 34 (10), 3058–65 (1991).
Derwent Abstract of WO/92128 (1992).

*Primary Examiner*—Cecilia Tsang
*Attorney, Agent, or Firm*—Frank S. Ungemach

[57] ABSTRACT

Certain nitrogen-containing cyclohetero cycloalkylaminoaryl compounds are described for treatment of CNS disorders such as cerebral ischemia, psychoses and convulsions. Compounds of particular interest are of the formula:

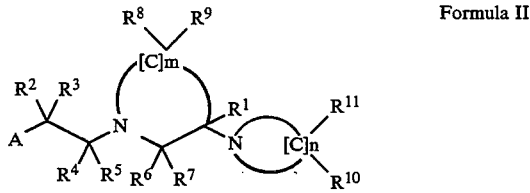

Formula II wherein each of $R^1$, $R^4$, $R^5$, $R^6$ and $R^7$ is independently selected from hydrido, lower alkyl, benzyl, and haloloweralkyl; wherein each of $R^2$, $R^3$ and $R^8$ through $R^{11}$ is independently selected from hydrido, hydroxy, loweralkyl, benzyl, phenoxy, benzyloxy and haloloweralkyl; wherein n is an integer of from four to six; wherein m is an integer of from two to four; wherein A is selected from phenyl, naphthyl, benzothienyl, benzofuranyl and thienyl; wherein any of the foregoing A groups can be further substituted with one or more substituents independently selected from hydrido, hydroxy, loweralkyl, loweralkoxy, halo, haloloweralkyl, amino, monoloweralkylamino and diloweralkylamino; or a pharmaceutically acceptable salt thereof.

12 Claims, No Drawings

NITROGEN-CONTAINING CYCLOHETERO CYCLOHETEROAMINOARYL DERIVATIVES FOR CNS DISORDERS

FIELD OF THE INVENTION

This invention is in the field of clinical neurology and relates specifically to a class of therapeutically useful compounds, compositions and methods for treatment of Central Nervous System (CNS) dysfunctions, neurotoxic damage, or neurodegenerative diseases. For example, these compounds are particularly useful for treating neurotoxic injury which follows periods of hypoxia, anoxia or ischemia associated with stroke, cardiac arrest or perinatal asphyxia. These compounds are also useful as antipsychotics and anticonvulsives.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman and J. W. Olney, "Glutamate and the Pathophysiology of Hypoxia-Ischemic Brain Damage," *Annals of Neurology*, 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS).

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with hypoxia, anoxia, or ischemia caused by stroke, cardiac arrest or perinatal asphyxia.

It is known that compounds of various structures, such as aminophosphonovalerate derivatives and piperidine dicarboxylate derivatives, may act as competitive antagonists at the NMDA receptor. Certain piperidineethanol derivatives, such as ifenprodil and 1-(4-chlorophenyl)-2-[1-(4-fluorophenyl)-piperidinyl]ethanol, which are known anti-ischemic agents, have been found to be non-competitive NMDA receptor antagonists [C. Carter et al, *J. Pharm Exp. Ther.*, 247 (3), 1222–1232 (1988)].

There are many classes of compounds known for treatment of psychotic disorders. For example, current therapeutic treatments for psychoses use compounds classifiable as phenothiazine-thioxanthenes, as phenylbutylpiperidines and also as certain alkaloids. An example of a phenylbutylpiperidine compound of current use in psychotic treatment therapy is haloperidol [A. F. Gilman et al, *The Pharmacological Basis of Therapeutics*, 7th Edn., p. 404, MacMillan (1985)].

Certain nitrogen-containing cyclohetero cycloalkylaminoaryl compounds are known for pharmaceutical purposes. For example, U.S. Pat. No. 4,204,003 to Szmuszkovicz describes N-(2-aminocyclopentyl)-N-alkanoylanilides as antidepressant agents.

Certain aminocycloaliphatic benzamides have been described for various uses. For example, U.S. Pat. No. 4,463,013 to Collins et al describes aminocyclohexylbenzamides for use as diuretic agents. The compound (±)-trans-3,4-dichloro-N-methyl-N-[2-(1-pyrrolidinyl)-cyclohexyl]-benzeneacetamide has been evaluated for its selectivity as an amino acid antagonist [C. G. Parsons et al, *Neuropharm.*, 25(2), 217–220 (1986)]. This same compound has been evaluated for its neuroprotective activity against kainate-induced toxicity [W. Lason et al, *Brain Res.*, 482, 333–339 (1989)]. U.S. Pat. No. 4,801,604 to Vonvoightlander et al describes certain cis-N-(2-aminocycloaliphatic)benzamides as anticonvulsants including, specifically, the compound cis-3,4-dichloro-N-methyl-N-[2-(1-pyrrolidinyl)cyclohexyl]-benzamide. Certain of these trans benzeneacetamide derivatives, such as trans-3,4-dichloro-N-methyl-N-[2-(1-pyrrolidinyl)cyclohexyl]benzeneacetamide, have been described as highly selective ligands for kappa opioid receptors. The cis isomers of 3,4-dichloro-N-methyl-N-[2-(1-pyrrolidinyl)cyclohexyl]-benzeneacetamide were identified to be potent and selective sigma ligands [B. R. de Costa et al, *J. Med. Chem.*, 32(8), 1996–2002 (1989)]. Further structure activity studies with these compounds resulted in the identification of (+)- and (−)-cis-N-[3,4-dichlorophenylethyl]-N-methyl-2-(1-pyrrolidinyl)-cyclohexylamines as extremely potent and selective ligands for the sigma receptor. These (Contreras et al, Brain Res.) and related (ethylenediamines) compounds (Long et al, INRC abstract) were found to be effective as protective agents for the damaging effects of ischemia and stroke in two different models of ischemia. See, for example, Long, J. B.; Tortella, F. C.; Rice, K. C.; de Costa B. R.: Selective Sigma ligands protect against dynorphin A-induced spinal cord injury in rats. *Soc. Neurosci. Abs.* 1990 16, 1122, abs 461.4; Contreras, P. C.; Ragan, D. M.; Bremer, M. E.; Lanthorn, T. H.; Gray, N. M.; Iyengar, S.; Jacobson, A. E.; Rice, K. C.; de Costa, B. R.: Evaluation of 450488H Analogs for antiischemic activity in the gerbil. *Brain Res.* 1991, 546, 79–82. Since these initial findings, neuroprotective activity has been identified among certain other high affinity sigma ligands. It is likely that the protective effects of these and related compounds is mediated through their interaction with the sigma receptor. Scopes et al., *J. Med. Chem.*, 35, 490–501 (1992) describe certain 2-[(alkylamino)methyl]-piperidines. In particular, 1-[(3,4-dichlorophenyl- )acetyl]-2[(alkylamino)methyl]piperidines are described as having activities as kappa opoid receptor agonists.

Treatment of CNS disorders and diseases such as cerebral ischemia, psychotic disorders and convulsions, as well as prevention of neurotoxic damage and neurodegenerative diseases, may be accomplished by administration of a therapeutically-effective amount of a compound of the formula:

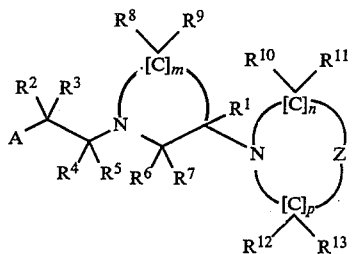

Formula I wherein each of $R^1$, $R^4$, $R^5$, $R^6$ and $R^7$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein each of $R^2$, $R^3$ and $R^8$ through $R^{13}$ is independently selected from hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl and alkynyl; wherein $R^2$ and $R^3$ may be taken together to form oxo or to form a saturated or partially unsaturated carbocyclic group having three to eight ring carbons; wherein $R^4$ and $R^5$ may be taken together to form a saturated or partially unsaturated carbocyclic group having three to eight ring carbons; wherein $R^8$ and $R^9$ may be taken together to form oxo; wherein $R^{10}$ and $R^{11}$ may be taken together to form oxo; wherein each of m, n and p is an integer of from one to four;
wherein Z is selected from

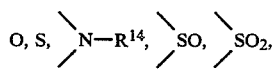

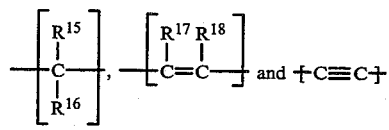

wherein $R^{14}$ may be selected from hydrido, alkyl, cycloalkyl, cycloalkylalkyl, aryl, aralkyl, heteroaryl, alkanoyl, aralkanoyl, aroyl, aminoalkyl, monoalkylaminoalkyl and dialkylaminoalkyl; wherein each of $R^{15}$ through $R^{18}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically-acceptable salt thereof.

A preferred family of compounds of Formula I consists of those compounds wherein each of $R^1$, $R^4$, $R^5$, $R^6$ and $R^7$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein each of $R^2$, $R^3$ and $R^8$ through $R^{13}$ is independently selected from hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl and alkynyl; wherein $R^2$ and $R^3$ may be taken together to form oxo or to form a saturated or partially unsaturated carbocyclic group having three to eight ring carbons; wherein $R^4$ and $R^5$ may be taken together to form oxo or to form a saturated or partially unsaturated carbocyclic group having three to eight ring carbons; wherein each m, n and p is an integer of from one to four; wherein Z is selected from

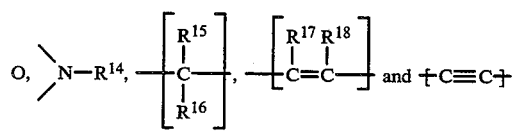

wherein $R^{14}$ may be selected from hydrido, alkyl, cycloalkyl, cycloalkylalkyl, aryl, aralkyl, heteroaryl, alkanoyl, aralkanoyl and aroyl; wherein each of $R^{15}$ through $R^{18}$ is independently selected from hydrido, alkyl, cycloalkyl, cycloalkylalkyl, aralkyl, aryl, alkoxyalkyl, haloalkyl, hydroxyalkyl, halo, cyano, carboxy, carboxyalkyl and alkanoyl; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically acceptable salt thereof.

A more preferred family of compounds within Formula I consists of those compounds wherein each of $R^1$, $R^4$, $R^5$, $R^6$ and $R^7$ is independently selected from hydrido, loweralkyl, cycloalkyl of three to about eight carbon atoms, phenylloweralkyl, phenyl, loweralkoxyloweralkyl, haloloweralkyl; hydroxyloweralkyl, carboxy, carboxyloweralkyl, loweralkanyl, loweralkenyl, loweralkynyl; wherein $R^2$, $R^3$ and $R^8$ through $R^{13}$ is independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenylloweralkoxy, loweralkoxyloweralkyl, haloloweralkyl, hydroxyloweralkyl, cyano, amino, monoloweralkylamino, diloweralkylamino, carboxy, carboxyloweralkyl, loweralkanoyl, loweralkenyl and loweralkynyl; wherein $R^2$ and $R^3$ may be taken together to form a saturated or partially unsaturated carbocyclic group having three to eight ring carbons; wherein $R^4$ and $R^5$ may be taken together to form a saturated or partially unsaturated carbocyclic group having three to eight ring carbons; wherein each of n and m is a number selected from one through four; wherein each of m, n and p is an integer from one to four; wherein Z is selected from

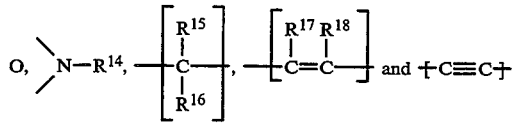

wherein $R^{14}$ may be selected from hydrido, loweralkyl, cycloalkyl of three to about eight carbon atoms, cycloalkylalkyl of four to about eight carbon atoms, phenyl, phenylloweralkyl, heteroaryl, loweralkanoyl, phenylalkanoyl, benzoyl, aminoloweralkyl, monoloweralkyl-aminoloweralkyl and diloweralkylamino-loweralkyl; wherein each of $R^{15}$ through $R^{18}$ is independently selected from hydrido, hydroxy, loweralkyl, cycloalkyl of three to about eight carbon atoms, cycloalkylalkyl of four to about eight carbon atoms, phenylloweralkyl, phenyl, loweralkoxyloweralkyl, haloloweralkyl, hydroxyloweralkyl, halo, cyano, amino, monoloweralkylamino, diloweralkylamino, carboxy, carboxyloweralkyl and loweralkanoyl; wherein A is selected from phenyl, naphthyl, heteroaryl, phenoxy, naphthyloxy, heteroaryloxy, phenylloweralkoxy, naphthylloweralkoxy, heteroarylloweralkoxy, phenylamino, naphthylamino, heteroarylamino, phenylloweralkylamino, naphthylloweralkylamino, heteroaralkylamino, phenylthio, naphthylthio, heteroarylthio, phenylloweralkylthio and heteroarylloweralkylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenylloweralkoxy, loweralkoxyloweralkyl, halo, haloloweralkyl, hydroxyloweralkyl, cyano, amino, monoloweralkylamino, diloweralkylamino, carboxy, carboxyloweralkyl, loweralkanoyl, loweralkenyl and loweralkynyl; or a pharmaceutically acceptable salt thereof.

A more highly preferred family of compounds of Formula I consists of those compounds wherein each of $R^1$, $R^4$, $R^5$, $R^6$ and $R^7$ is independently selected from hydrido, loweralkyl, cycloalkyl of three to about eight carbon atoms, cycloalkylalkyl of four to about eight carbon atoms, benzyl, phenyl, loweralkoxyloweralkyl, haloloweralkyl, hydroxyloweralkyl, loweralkanoyl, loweralkenyl, and loweralkynyl; wherein $R^2$, $R^3$ and $R^8$ through $R^{13}$ is independently selected from hydrido, hydroxy, loweralkyl, cycloalkyl of three to about eight carbon atoms, cycloalkylalkyl of four to about eight carbon atoms, benzyl, phenyl, loweralkoxy, phenoxy, benzyloxy, loweralkoxyloweralkyl, haloloweralkyl, hydroxyloweralkyl, loweralkanoyl, loweralkenyl and loweralkynyl; wherein $R^2$ and $R^3$ may be taken together to form a saturated or partially unsaturated carbocyclic group having three to eight ring carbons; wherein $R^4$ and $R^5$ may be taken together to form oxo or to form a saturated or partially unsaturated carbocyclic group having three to eight ring carbons; wherein each of m, n and p is an integer from one to four; wherein Z is selected from O, >N—$R^{14}$,

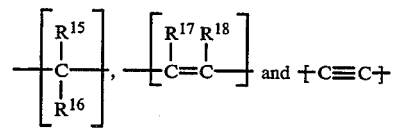

wherein $R^{14}$ may be selected from hydrido, loweralkyl, cycloalkyl of three to about eight carbon atoms, cycloalkylalkyl of four to about eight carbon atoms, phenyl and benzyl; wherein each of $R^{15}$ through $R^{18}$ is independently selected from hydrido, loweralkyl, cycloalkyl of three to about eight carbon atoms, cycloalkylalkyl of four to about eight carbon atoms, benzyl, phenyl, loweralkoxyloweralkyl, hydroxyloweralkyl and halo; wherein A is selected from phenyl, naphthyl, benzo[b]thienyl, thienyl, phenoxy, benzyloxy, naphthyloxy, thiophenoxy, phenylamino, benzylamino, naphthylamino, phenylthio, benzylthio and naphthylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, loweralkoxy, loweralkoxyloweralkyl, halo, haloloweralkyl, hydroxyloweralkyl, amino, monoloweralkylamino, diloweralkylamino, loweralkanoyl, loweralkenyl and loweralkynyl; or a pharmaceutically acceptable salt thereof.

A family of compounds of particular interest within Formula I are compounds embraced by Formula II:

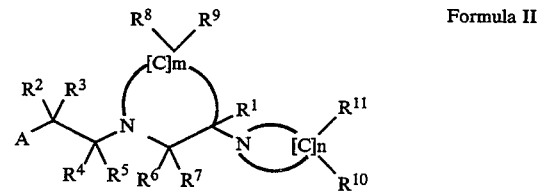

Formula II wherein each of $R^1$, $R^4$, $R^5$, $R^6$ and $R^7$ is independently selected from hydrido, loweralkyl, benzyl and haloloweralkyl; wherein $R^2$, $R^3$ and $R^8$ through $R^{11}$ is independently selected from hydrido, hydroxy, loweralkyl, benzyl, phenoxy, benzyloxy and haloloweralkyl; wherein n is an integer of from four to six; wherein m is an integer of from two to four; wherein A is selected from phenyl, naphthyl, benzothienyl, benzofuranyl and thienyl; wherein any of the foregoing A groups can be further substituted with one or more substituents independently selected from hydrido, hydroxy, loweralkyl, loweralkoxy, halo, haloloweralkyl, amino, monoloweralkylamino and diloweralkylamino; or a pharmaceutically acceptable salt thereof.

A more preferred family of compounds within Formula II consists of compounds wherein each of $R^1$, $R^4$, $R^5$, $R^6$ and $R^7$ is independently selected from hydrido, methyl, ethyl, propyl, benzyl and haloloweralkyl, wherein $R^2$, $R^3$ and $R^8$ through $R^{13}$ is independently selected from hydrido, hydroxy, methyl, ethyl, propyl, benzyl, phenoxy, benzyloxy and haloloweralkyl; wherein m is a number selected from four or five; wherein m is an integer of from two or three; wherein A is phenyl or naphthyl; wherein any of the foregoing A groups can be further substituted with one or more substituents independently selected from hydroxy, methyl, ethyl, propyl, methoxy, ethoxy, methylenedioxy, halo, trifluoromethyl, amino, methylamino and dimethylamino; or a pharmaceutically acceptable salt thereof.

Of highest interest are the following specific compounds:

3-(1-pyrrolidinyl)-N-(2-[3,4-dichlorophenyl]ethyl)-piperidine
3-(1-piperidinyl)-N-(2-[3,4-dichlorophenyl]ethyl)piperidine
3-(1-pyrrolidinyl)-N-(2-[3,4-dichlorophenyl]ethyl)-homopiperidine
3-(1-piperidinyl)-N-(2-[3,4-dichlorophenyl]ethyl)-homopiperidine
3-(1-pyrrolidinyl)-N-(2-[3,4-dichlorophenyl]ethyl)pyrrolidine
3-(1-piperidinyl)-N-(2-[3,4-dichlorophenyl]ethyl)pyrrolidine
3-(1-homopiperidinyl)-N-(2-[3,4-dichlorophenyl]ethyl)-piperidine
3-(1-homopiperidinyl)-N-(2-[3,4-dichlorophenyl]ethyl)-homopiperidine
3-(1-homopiperidinyl)-N-(2-[3,4-dichlorophenyl]ethyl)-pyrrolidine
3-(1-homopiperidinyl)-N-(2-[3-benzothienyl]ethyl)-piperidine
3-(1-homopiperidinyl)-N-(2-[3-benzothienyl]ethyl)-homopiperidine
3-(1-homopiperidinyl)-N-(2-[3-benzothienyl]ethyl)pyrrolidine
3-(1-homopiperidinyl)-N-(2-[2-naphthyl]ethyl)piperidine
3-(1-homopiperidinyl)-N-(2-[1-naphthyl]ethyl)-homopiperidine
3-(1-homopiperidinyl)-N-(2-[3-naphthyl]ethyl)pyrrolidine
3-(1-piperidinyl)-N-(2-[3-benzothienyl]ethyl)piperidine
3-(1-pyrrolidinyl)-N-(2-[3-benzothienyl]ethyl)piperidine
3-(1-piperidinyl)-N-(2-[3-benzothienyl]ethyl)pyrrolidine
3-(1-pyrrolidinyl)-N-(2-[3-benzothienyl]ethyl)pyrrolidine
3-(1-piperidinyl)-N-(2-[3-benzothienyl]ethyl)-homopiperidine
3-(1-pyrrolidinyl)-N-(2-[3-benzothienyl]ethyl)-homopiperidine The term "hydrido" denotes a single hydrogen atom (H) which may be attached, for example, to an oxygen atom to form hydroxyl group. Where the term "alkyl" is used, either alone or within other terms such as "haloalkyl" and "hydroxyalkyl", the term "alkyl" embraces linear or branched radicals having one to about twenty carbon atoms or, preferably, one to about ten carbon atoms. More preferred alkyl radicals are "lower alkyl" radicals having one to about five carbon atoms. The term "cycloalkyl" embraces cyclic radicals having three to about six carbon atoms, such as cyclopropyl and cyclobutyl. The term "haloalkyl" embraces radicals wherein any one or more of the alkyl carbon atoms is substituted with one or more halo groups, preferable selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. An example of a polyhaloalkyl is a trifluoromethyl group. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferable two to about ten carbon atoms, and containing at least one carbon-carbon triple bond. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl including benz-fused systems such as benzothienyl, 2-quinolinyl and the like. The term "alkylene chain" describes a chain of two to six methylene ($-CH_2-$) groups which may form a cyclic structure with or without a hetero atom in the cyclic structure.

Specific examples of alkyl groups are methyl, ethyl, n-propyl, isopropyl, n-butyl, sec-butyl, iso-butyl, tert-butyl, n-pentyl, iso-pentyl, methyl-butyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Included within the family of compounds of Formulas I–II are the tautomeric forms of the described compounds, isomeric forms including enantiomers and diastereoisomers, and the pharmaceutically-acceptable salts thereof. The term "Pharmaceutically-acceptable salts" embraces salts commonly used to form alkali metal salts and to form addition salts of free acids or free bases. Since the compounds of Formulas I–II contain basic nitrogen atoms, such salts are typically acid addition salts. The phrase "pharmaceutically-acceptable salts" is not intended to embrace quaternary ammonium salts. The nature of the salt is not critical, provided that it is pharmaceutically acceptable, and acids which may be employed to form salts are, of course, well known to those skilled in this art. Examples of acids which may be employed to form pharmaceutically acceptable acid addition salts include such inorganic acids as hydrochloric acid, sulfuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of Formulas I–II in a suitable solvent (e.g. methanol).

GENERAL SYNTHETIC PROCEDURES

Compounds of Formulas I and II may be prepared in accordance with the following generic procedures, within which specific schemes are shown for Formula II type compounds.

Step 1

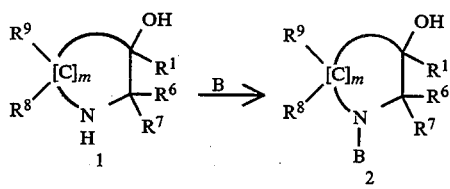

wherein $R^1$, $R^6$ through $R^9$, and m are as defined previously; and wherein B represents a protecting group such as acetyl, benzoyl, t-butyloxycarbonyl or benzyloxycarbonyl.

A process for preparing the compounds of the invention starts with hydroxy-substituted cycloaminoalkyl compounds of general structure 1 where $R^1$, $R^6$ through $R^9$, and m have the value assigned previously. An example of a compound within the general structure 1 is 3-hydroxypiperidine. The amino group of 1 is protected employing protecting groups such as acetyl, benzoyl, t-butoxycarbonyl or benzyloxycarbonyl or other amino protecting groups familiar to those skilled in the art. This protection can be achieved by reacting the protecting group as the chloride or anhydride in organic solvents and at temperatures ranging from −60° to reflux of the reaction mixture.

Step 2

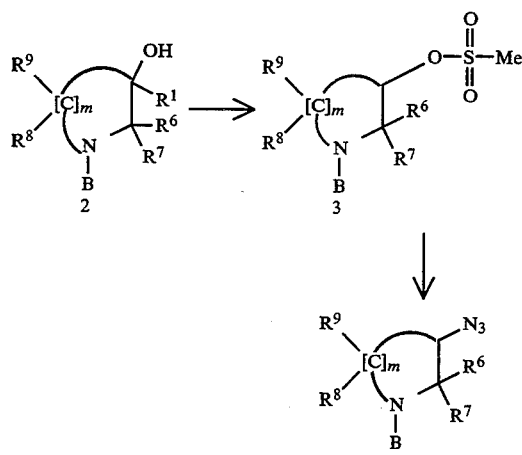

wherein B, $R^1$, $R^6$, $R^7$, $R^{10}$, $R^{11}$, n, and q are as defined previously.

In the second step of the process, the hydroxyl group of the N-protected compounds of general structure 2 are converted to the corresponding azides of general structure 4 through the corresponding methanesulfonate ester of general structure 3 where B, $R^1$, $R^6$, $R^7$, $R^8$, $R^9$ and m are as defined previously. The compounds can be combined neat or in a variety of solvents such as tetrahydrofuran. For example, treatment of a stirred solution of 2 in dry THF at ambient temperature containing triethylamine (3 molar equivalents) with methanesulfonyl chloride (1.2 molar equivalents) afforded 3. This was isolated by standard methods familiar to those skilled in the art. The methanesulfonate ester 3 was dissolved in dry DMF and heated and stirred (70° C., overnight) with excess sodium azide (3–5 molar equivalents). The product 4 was isolated by standard methods familiar to those skilled in the art. The temperature of the reaction can vary from room temperature to reflux of the reaction mixture.

Step 3

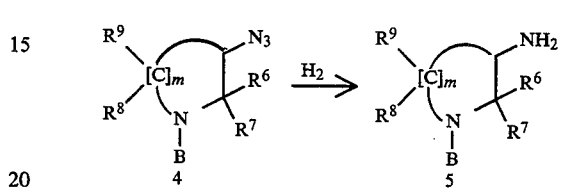

wherein B, $R^1$, $R^6$, $R^7$, $R^8$, $R^9$ and m are as defined previously.

In the third step of the process, azides of general structure 4 are reduced to amines of general structure 5 by employing catalytic hydrogenation, or other reducing agents familiar to those skilled in the art. This reduction can be accomplished in either protic or aprotic solvents, depending on the reducing agent of choice, and at temperatures ranging from room temperature to reflux of the reaction mixture.

Step 4

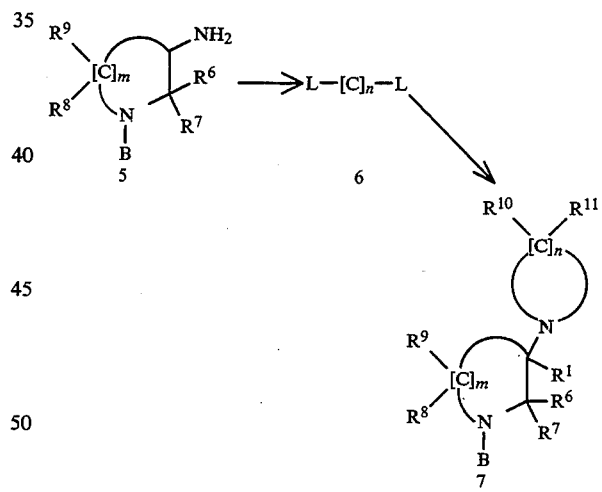

wherein B, $R^1$, $R^6$, $R^7$, $R^{10}$, $R^{11}$, m, and n are as defined previously and wherein L denotes a suitable leaving group such as a halide, e.g. Cl or Br or methanesulfonate or p-toluene-sulfonate.

In the fourth step of the process, the amines of general structure 5 are converted to amines of general structure 7 by reaction with compound 6. The conversion is best achieved by mixing 5 with 1,4-dibromobutane or 1,5-dibromopentane in dry DMF followed by later addition of 1.2 molar equivalents of potassium carbonate. The temperature of the reaction can vary from room temperature to reflux of the reaction mixture.

Step 5

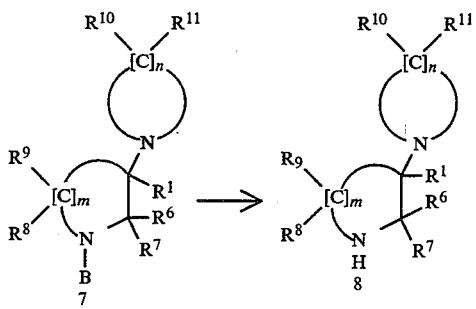

In the fifth step, the amino protecting group B is removed by mixing 7 with a suitable acid such as trifluoroacetic acid, hydrochloric acid, and the like which are familiar to those skilled in the art. Alternatively, the amino protecting group is removed by mixing 7 with a suitable base such as sodium hydroxide, potassium hydroxide and the like, which are familiar to those skilled in the art. The compounds are mixed in a suitable solvent, preferably a protic solvent such as water ethylene glycol or methanol. Alternatively, in the case of the benzyloxycarbonyl group, deprotection can be achieved by catalytic hydrogenation in the presence of a suitable catalyst such as 10% palladium on carbon in a suitable solvent such as methanol. The temperature of the reaction can vary from room temperature to reflux of the reaction mixture.

Step 6

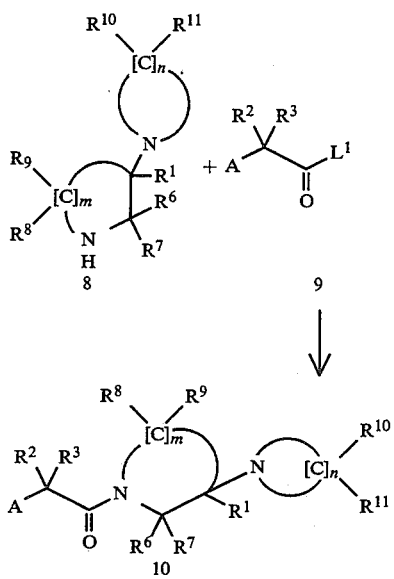

wherein A, $R^1$, $R^2$, $R^3$, $R^6$ through $R^{11}$, m and n are as defined previously; and wherein $L^1$ is a good leaving group such as chloro, bromo, acyloxy, or "activated" hydroxy.

In the sixth step of the process, amines of general structure 8 are converted to amides of general structure 10 where A, $R^2$, and $R^3$ have the value assigned previously and $L^1$ is a good leaving group such as chloro, bromo, acyloxy, or "activated" hydroxy. The conversion can be best achieved by mixing the reagents neat or in a protic solvent such as tetrahydrofuran, methylene chloride, or ether in the presence of a base such as triethylamine. The reaction can be run in the absence or presence of an activating agent such as dicyclohexylcarbodiimide or phosphorus oxychloride, depending on the leaving group of choice. The temperature of the reaction can vary from 0° to reflux of the reaction mixture.

Step 7

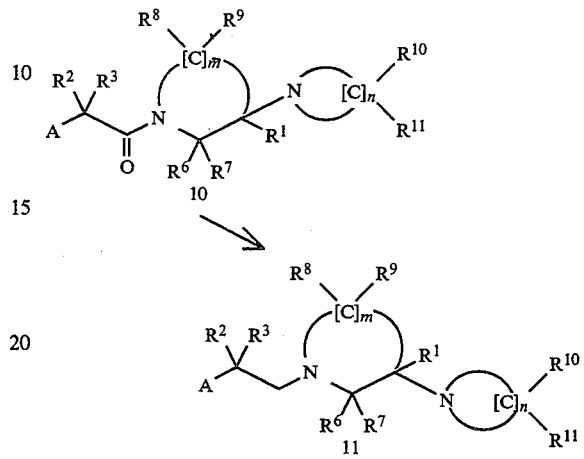

wherein A, $R^1$, $R^2$, $R^3$, $R^6$ through $R^{11}$, m and n are as defined previously.

In the seventh step of the process, amides of general structure 10 are converted to amines of general structure 11 by employing reducing agents such as lithium aluminum hydride, aluminum hydride, sodium borohydride, sodium cyanoborohydride, or other reducing agents familiar to those skilled in the art. This reduction can be accomplished in either protic or aprotic solvents, depending on the reducing agent of choice, and at temperatures ranging from room temperature to reflux of the reaction mixture.

Step 6(b)

Alternately, amines of general structure 11 can be prepared according to the following generic procedure.

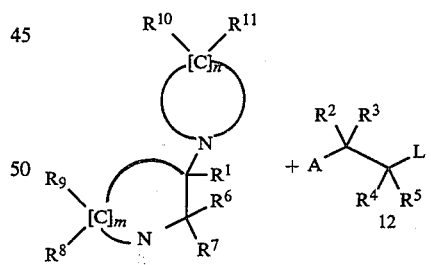

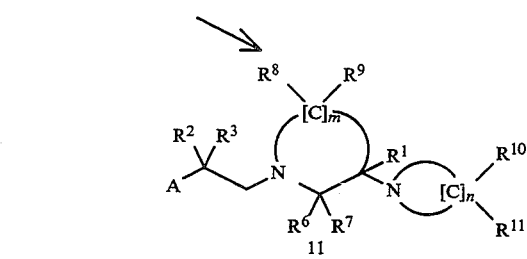

wherein A, $R^1$ through $R^{11}$ and m and n are as defined previously; and wherein $L^2$ is a good leaving group such as halogen, tosylate, mesylate, or brosylate.

Amines of general structure 13 can be alternately prepared by combining amines of general structure 8 with compounds of general structure 12 where A, R¹ through R¹¹, m and n have the values assigned previously and where L² is a good leaving group such as halogen, tosylate, mesylate, or brosylate. The compounds can be combined in a variety of solvents such as toluene, xylenes, dimethylformamide, hexamethylphosphoramide, or ethanol. The temperature of the reaction can vary from room temperature to reflux of the reaction mixture.

The scheme set forth below sets forth a more detailed scheme for preparing 3-aminopiperidine-containing compounds of the present invention.

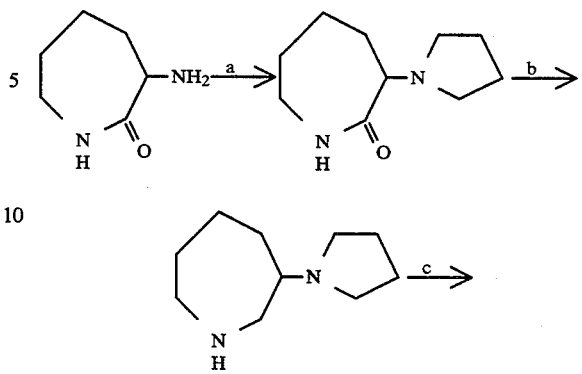

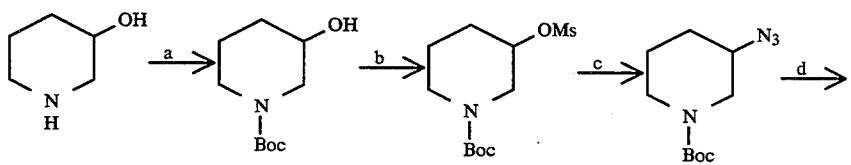

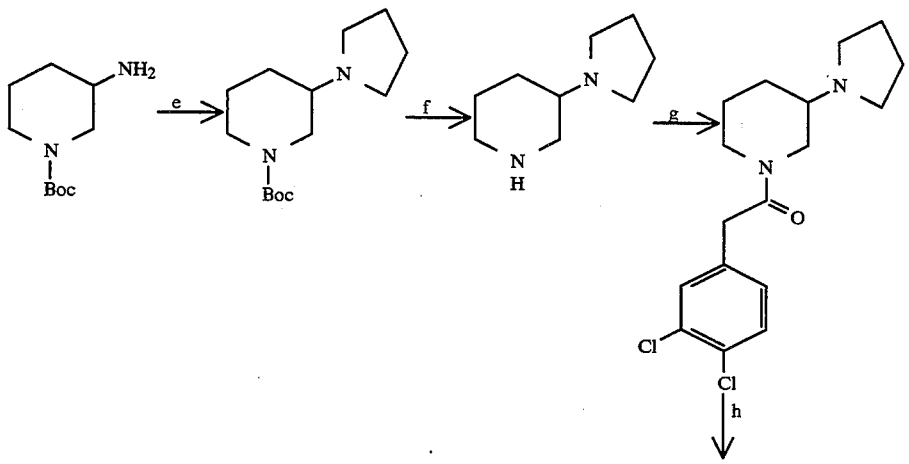

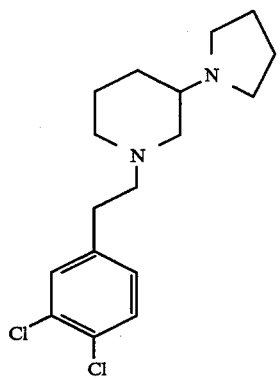

a: (Boc)₂O, aq NaHCO₃, r.t.; b: MeSO₃Cl, THF, Et₃N; c: NaN₃, DMF, 70° C.; d: H₂, 10% Pd/C, MeOH-AcOH (1:1); e: 1,4-dibromobutane, K₂CO₃, DMF, 55° C.; f: CF₃COOH, r.t.; g: 3,4-dichlorophenylacetic acid, DCC, CH₂Cl₂, r.t.; h: AlH₃, THF, r.t.

The scheme set forth below sets forth a more detailed scheme for preparing 3-aminohomopiperidine-containing compounds of the present invention.

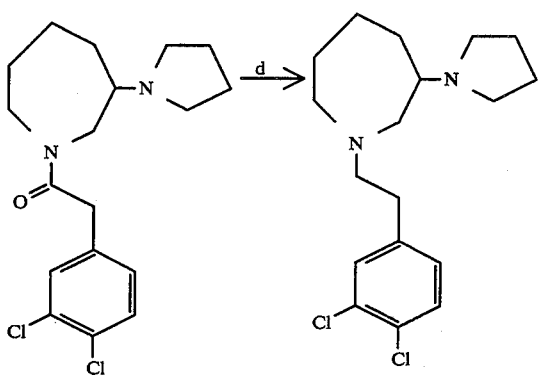

a: 1,4-dibromobutane, K$_2$CO$_3$, DMF, 55° C.; b: LiAlH$_4$, THF, reflux; c: 3,4-dichlorophenylacetic acid, DCC, CH$_2$Cl$_2$, r.t.; d: AlH$_3$, THF, r.t.

The following Examples are detailed descriptions of the methods of preparation of compounds of Formula I. These detailed preparations fall within the scope of, and serve to exemplify, the above described Generic Procedures which form part of the invention. These Examples are presented for illustrative purposes only and are not intended as a restriction on the scope of the invention. All parts are by weight unless otherwise indicated. Most of the commercially available starting materials were obtained from Aldrich Chemical Company, Milwaukee, Wis.

Melting points were determined on a Thomas-Hoover capillary apparatus and are uncorrected. Specific rotation determinations at the sodium-D line were obtained in a 1 dM cell using a Perkin-Elmer 241-MC polarimeter. Elemental analyses were performed at Atlantic Microlabs, Atlanta, Ga.; where molecular formulae are indicated followed by the symbols of the elements, analyses are within ±0.4% of the theoretical values. Chemical-ionization mass spectra (CIMS) were obtained using a Finnigan 1015 mass spectrometer. Electron ionization mass spectra (EIMS) and high resolution mass measurements (HRMS) were obtained using a VG-Micro Mass 7070F mass spectrometer. $^1$H-NMR spectra were measured from CDCl$_3$ solutions using a Varian SL-300 spectrometer. Thin layer chromatography (TLC) was performed on 250 μM Analtech GHLF silica gel plates. TLC system A corresponds to CHCl$_3$-MeOH-conc. aq. NH$_3$ (90:9:1). TLC system B corresponds to CHCl$_3$-MeOH-conc. aq. NH$_3$ (80:18:2). TLC system C corresponds to EtOAc/hexanes (1:2). No attempt was made to optimize the yields. For purposes of clarity, enantiomeric compounds are indicated with prefixes indicating absolute configuration and/or the direction of rotation whereas racemic compounds are shown without prefixes.

EXAMPLE 1

1-(tert-Butoxycarbonyl)-3-(hydroxy)piperidine

To a stirred solution of 3-hydroxypiperidine (25.0 g, 247 mmol) and NaHCO$_3$ (62.3 g, 742 mmol, 3 eq) in water (500 mL) was added di-t-butoxydicarbonate (64.7 g, 296 mmol, 1.2 eq) and the solution was stirred for 48 h at rt. The aqueous mixture was extracted with CH$_2$Cl$_2$ (3×200 mL). The combined organic extract was back-washed with water (50 mL) and dried by filtration through Na$_2$SO$_4$. Evaporation of the solvent afforded the desired product as a colorless oil. Distillation under high vacuum (140° C./1.2 mmHg) afforded the product as an oil which crystallized on standing (45.5 g, 92%): mp 70°–72° C.; 1H-NMR (CDCl$_3$) ∂ 3.73 (d, J=10 Hz, 2H), 3.52 (m, 1H), 3.12 (m, 2H), 1.88 (m, 1H), 1.76 (m, 1H), 1.19–1.66 (complex m, 2H), 1.46 (s, 9H); CIMS (MH+ calcd for C$_{10}$H$_{19}$NO$_3$): 202. Found (MH+): 202 Anal. (calcd for C$_{10}$H$_{19}$NO$_3$): C, H, N.

EXAMPLE 2

1-(tert-Butoxycarbonyl)-3-(methanesulfonyloxy)piperidine

To a stirred solution of the title compound of Example 1 (44.3 g, 220 mmol) and Et$_3$N (61.4 mL, 440 mmol, 2 eq) in THF (250 mL) was added dropwise at rt (maintained by cooling from an ice bath), methanesulfonyl chloride (27.77 g, 242 mmol, 1.1 eq). The reaction mixture was stirred for 1 h at rt when TLC (solvent system C) indicated completion. The precipitated Et$_3$NHCl was removed by filtration and the filter cake was washed with 50 mL of THF. The combined flitrate and washings were evaporated in vacuo to give the crude product as a yellow oil. This was dissolved in EtOAc/hexanes (1:2) and passed through a pad of silica gel eluting with ethyl acetate/hexanes (1:3). Evaporation of the flitrate afforded the product as a pale yellow oil (59.1 g, 96%) which crystallized on standing. Recrystallization from EtOAc/hexane (1:10) afforded an analytically pure sample of the title compound: mp 69°–70° C.; $^1$H-NMR (CDCl$_3$) ∂ 4.72 (m,1H), 3.63 (m, 2H), 3.46 (m, 1H), 3.32 (m, 1H), 3.05 (s, 3H), 1.75–2.06 (complex m, 4H), 1.46 (s, 9H); CIMS (MH+ calcd for C$_{11}$H$_{21}$NO$_5$S): 280. Found (MH+): 280; Anal. (calcd for C$_{11}$H$_{21}$NO$_5$S): C, H, N.

EXAMPLE 3

3-Azido-1-(tert-butoxycarbonyl)piperidine

A mixture of the title compound of Example 2 (45.1 g, 205 mmol) and NaN$_3$ (39.9 g, 614 mmol, 3.0 eq) in DMF (200 mL) was heated and stirred at 70° C. for 48 h when TLC (solvent system C) indicated the reaction to be complete. The reaction mixture was cooled to rt and poured into cold water (200 mL). The aqueous mixture was extracted with Et$_2$O (500 mL) and the organic extract was back-washed with water (2×100 mL), dried (Na$_2$SO$_4$) and the solvent was evaporated in vacuo to afford the title compound (45.5 g, 98%) as a colorless oil: $^1$H-NMR (CDCl$_3$) ∂ 3.66–3.80 (m, 1H), 3.57 (m, 1H), 3.45 (m, J$_{app}$=4.0 Hz, 1H), 3.12 (m, 2H), 1.90–2.05 (m, 2H), 1.69–1.83 (m, 2H), 1.47 (s, 9H).

EXAMPLE 4

3-Amino-1-(tert-butoxycarbonyl)piperidine

A solution of the title compound of Example 3 (37.1 g, 164 mmol) in a mixture of MeOH (100 mL) and acetic acid (25 mL) was added 10% Pd-C (3.7 g) and the reaction mixture was hydrogenated (50 psi) for 24 h at rt in a Parr apparatus. Analysis of the reaction by TLC (solvent system A) and IR (to look for presence or absence of N$_3$ str peak at 2100 cm$^{-1}$) indicated the reaction to be complete. The solution was filtered through celite to remove catalyst and the filtrate was evaporated in vacuo to give the crude product as an oily residue. The residue was dissolved in 500 mL of 10% aqueous acetic acid and the solution was extracted with Et$_2$O (3×200 mL). The combined ethereal extract was discarded and the aqueous solution was basified by addition of excess concentrated aqueous $NH_3$ solution. The basified mixture was extracted with $Et_2O$ (3×200 mL) and the combined organic extract was dried ($Na_2SO_4$) and evaporated to give the title compound (22.8 g, 69%) as a pale yellow oil. The fumarate salt crystallized from 2-propanol: mp 197°–198° C., $^1H$-NMR ($CDCl_3$) ∂ 3.93 (br s, 1H), 3.82 (dm, $J_{gem}=13$ Hz, 1H), 1.46 (s, 9H), 1.29–1.41 (complex m, 3H), 1.24 (m, 1H); CIMS (MH+ calcd for $C_{10}H_{20}N_2O_2$): 201. Found (MH+): 201; Anal. (calc'd for $C_{10}H_{20}N_2O_2.0.5C_4H_4O_4$):C, H, N.

EXAMPLE 5

1-(tert-Butoxycarbonyl)-3-(1-pyrrolidinyl)piperidine

To a stirred solution of the base obtained from the fumarate salt of the title compound of Example 4 (3.00 g, 9.49 mmol) in DMF (25 mL) was added butane-1,4-dibromide (2.25 g, 10.4 mmol, 1.1 eq) and the solution was stirred at 55° C. for 48 h under a $N_2$ atmosphere. Anhydrous $K_2CO_3$ (1.44 g, 10.4 mmol, 1.1 eq) was added and stirring and heating (55° C.) was continued for a further 24 h. The reaction mixture was cooled, poured into 10% $K_2CO_3$ (120 mL) and the aqueous mixture was extracted with $Et_2O$ (2×150 mL). The combined organic extract was extracted with 10% citric acid (200 mL). The citric acid extract was washed with a further 2×150 mL of $Et_2O$ and the combined organic layer was discarded. The aqueous extract was basified by the addition of excess aqueous $NH_3$ and then extracted with $CH_2Cl_2$ (3×100 mL). The combined $CH_2Cl_2$ extract was dried ($Na_2CO_3$) and the solvent evaporated in vacuo to afford the title compound (2.41 g, quantitative) as a colorless oil. The fumarate salt crystallized from EtOAc: mp 136°–138° C.; $^1H$-NMR ($CDCl_3$) ∂ 3.94 (br d, $J_{gem}=13$ Hz, 1H), 2.48–2.80 (complex m, 6H), 2.06 (m, 2H), 1.60–1.84 (complex m, 6H), 1.46 (s, 9H), 1.30–1.50 (m, 2H); CIMS (MH+ calcd for $C_{14}H_{26}N_2O_2$): 255. Found (MH+): 255; Anal. (calcd for $C_{18}H_{30}N_2O_6$): C, H, N.

EXAMPLE 6

3-(1-Pyrrolidinyl)piperidine

The fumarate of the title compound of Example 5 (2.00 g, 5.40 mmol) was suspended in $CHCl_3$ (20 mL) and the solution was treated with $CF_3COOH$ (25 mL). TLC (solvent system A) indicated the reaction to be complete after 10 min at rt. The solvent was evaporated in vacuo and the residue was dissolved in cold (5° C.) 50% aqueous NaOH (100 mL) and extracted with $CHCl_3$ (2×100 mL). The combined organic layer was dried ($Na_2SO_4$) and the solvent was evaporated in vacuo to give the title compound (0.80 g, quantitative) as a colorless oil. The HBr salt of the title compound crustallized from 2-propanol: mp 217°–218° C.; $^1H$-NMR ($CDCl_3$) ∂ 3.22 (dm, $J_{gem}+11$ Hz, 1H), 2.94 (dm, $J_{gem}+12$ Hz, 1H), 2.48–2.62 (complex m, 6H), 1.98–2.11 (complex m, 2H), 1.65–1.82 (complex m, 6H), 1.30–1.54 (complex m, 2H); CIMS (calcd for $C_9H_{18}N_2$): 155. Found (MH+): 155; Anal. (calcd for $C_9H_{20}Br_2N_2$): C, H, N.

EXAMPLE 7

3-(1-Pyrrolidinyl)-1-(3,4-dichlorophenylacetyl)piperidine

To a stirred solution of 3,4-dichlorophenylacetic acid (2.0 g, 9.75 mmol, 1.5 eq) in $CH_2Cl_2$ (50 mL) was added a solution of DCC (2.68 g, 13.0 mmol, 2 eq) in $CH_2Cl_2$ (50 mL). The mixture was stirred at rt for 10 min during which time a white precipitate formed. To this was added the free-base form of title compound of Example 6 (1.0 g, 6.5 mmol). The reaction mixture was stirred for 10 min at rt or until TLC (solvent system A) indicated reaction to be complete, The precipitated dicyclohexylurea (DCU) was removed by filtration and washed with a little (10 mL) ether. The combined flitrate and washings were diluted to 200 mL with ether and extracted with 10% aqueous citric acid (100 mL). The organic layer was discarded and the aqueous citric acid layer was washed with ether (3×50 mL) and basified with excess concentrated aqueous $NH_3$ soluution. The basified solution was extracted with $CH_2Cl_2$ (2×100 mL) and the combined organic extract was backwashed with water (50 mL), dried ($Na_2SO_4$) and the solvent was evaporated in vacuo to give the title compound (2.2 g, quantitative) as an oil. Crystallization of the oxalate salt from 2-propanol afforded crystals: mp 134°–135° C. $^1H$-NMR ($CDCl_3$) ∂ 7.40 (43%), 7.37 (57%) (d, J=8.2 Hz, 1H), 7.36 (d, J=2.4 Hz, 1H), 7.11 (dm, J=8.2 Hz, 1H), 4.50 (dm, J=13 Hz, 1H), 3.60–4.0 (m, 1H), 3.68 (s, 2H), 2.73–3.10 (complex m, 2H), 2.62 (m, 2H), 2.50 (m, 2H), 2.04 (m, 2H), 1.65–1.95 (complex m, 5H), 1.43 (m, 2H); CIMS (MH+ calcd for $C_{16}H_{22}Cl_2N_2O$): 341. Found (MH+): 341; Anal. (calcd for $C_{19}H_{24}Cl_2N_2O_5$): C, H, N.

EXAMPLE 8

3-(1-Pyrrolidinyl)-1-[2-(3,4-dichlorophenyl)ethyl]-piperidine

A solution of the title compound of Example 7 (1.1 g, 3.23 mmol) in dry THF (20 mL) was added dropwise at rt to a stirred solution of $AlH_3$ in THF (24.4 mL of a 0.66M solution, 16.1 mmol, 5 eq). The reaction mixture was stirred for 20 min at rt and then poured into 15% aqueous NaOH (100 mL) and extracted with $CHCl_3$ (300 mL). The organic layer was dried ($Na_2SO_4$) and the solvent was evaporated in vacuo to give the crude product as a colorless oil. 5.HBr (0.96 g, 61%) (EtOH): mp 279°–280° C.; $^1H$-NMR ($CDCl_3$) ∂ 7.33 (d, J=8.3 Hz, 1H), 7.29 (d, J=1.8 Hz, 1H), 7.03 (dd, J=1.8, 8.3 Hz, 1H), 3.08 (m, 1H), 2.84 (m, 1H), 2.76 (m, 2H), 2.51–2.66 (complex m, 6H), 2.25 (m, 1H), 2.00 (t, J=10 Hz, 2H), 1.50–1.83 (complex m, 7H), 1.26 (m, 1H); CIMS (MH+ calcd for $C_{17}H_{24}Cl_2N_2$): 327. Found (MH+): 327; Anal. (calcd for $C_{17}H_{26}Br_2Cl_2N_2$): C, H, N.

EXAMPLE 9

3-(1-Pyrrolidinyl)caprolactam

A mixture of D,L-alpha-aminocaprolactam (5.0 g, 39.0 mmol), 1,4-dibromobutane (8.42 g, 39.0 mmol, 1 eq) and $K_2CO_3$ (5.39 g, 39 mmol, 1.0 eq) was reacted in DMF (40 mL) as described above in Example 5 to give the title compound (4.58 g, 64%) as a colorless oil. The fumarate salt crystallized from 2-propanol: mp 215° C. (dec); 1H-NMR ($CDCl_3$) c 5.72 (br s, 1H, NH), 3.73 (m,1H), 2.96–3.10 (m, 2H), 2.68 (m, 2H), 2.53 (m, 2H), 1.46–2.05 (complex m, 10H); CIMS (MH+ calcd for $C_{10}H_{18}N_2O$): 183. Found (MH+): 183. HRMS (M+ clc'd for $C_{10}H_{18}N_2O$): 182.1419. Found (M+): 182.1413.

EXAMPLE 10

3-(1-Pyrrolidine)homopiperidine

The title compound of Example 9 (4.58 g, 25.2 mmol) was reduced with LiAlH$_4$ (50.4 mL of a 1.0M solution in THF, 50.4 mmol, 2 eq) to give the title compound (3.82 g, 90%) as a pale yellow oil. A solution of the title compound of Example 9 (10.8 g, 47.4 mmol) in THF (20 mL) was added dropwise at rt to a stirred solution of LiAlH$_4$ in THF (153 mL of a 1.0M solution, 153 mmol, 3.2 eq). The solution was stirred overnight at rt when TLC (solvent system B) indicated incomplete reduction. However, reduction was found to be complete after boiling under reflux for 4 h. The solution was stirred, cooled to 0° C. (ice bath) and treated dropwise with water (5.8 mL), 15% aqueous NaOH (5.8 mL) and finally water (17.4 mL). The mixture was stirred for 1 h and then filtered. Aqueous HCl was added (to pH=1) and the solvent was evaporated in vacuo to give the corresponding hydrochloride salt (8.28 g, 87%) as white crystals (2-propanol): mp 155°-156° C.; $^1$H-NMR (CDCl$_3$) ∂ 2.93 (d, J=5 Hz, 2H), 2.85 (m, 2H), 2.56 (m, 4H), 2.31 (m, 1H), 1.59-1.87 (complex m, 9H), 1.50 (m, 1H); CIMS (MH+ calcd for C$_{10}$H$_{20}$N$_2$): 169. MH+ (found): 169; EIMS M+ (C$_{10}$H$_{20}$N$_2$) requires: 168.1626. Found (M+): 168.1630.

EXAMPLE 11

1-(3,4-Dichlorophenylacetyl)-3-(1-pyrrolidinyl)-homopiperidine

The title compound of Example 10 (0,80 g, 4.76 mmol) was coupled with 3,4-dichlorophenylacetic acid (1.05 g, 5.12 mmol, 1.1 eq) in the presence of DCC (1.3 g, 6.30 mmol, 1.2 eq) as described for Example 7 to give the title compound in quantitative yield as a yellow oil. The fumarate salt crystallized from 2-propanol (1.66 g, 74%): mp 156°-158° C.; $^1$H-NMR (CDC$_{l3}$): ∂ 7.39 (d, J=8.3 Hz, 1H), 7.36 (d, J=2.0 Hz, 1H), 7.12 (40%), 7.10 (60%) (dd, J=2.0, 8.3 Hz, 1H), 4.32 (40%) (d, J$_{gem}$=13 Hz, J=3.7 Hz, 1H), 3.54-3.87 (complex m, 5H), 3.30 (m, 2H), 2.94 (m, 1H), 2.36-2.84 (complex m, 4H), 1.18-1.96 (complex m, 9H); CIMS (MH+ calcd for C$_{18}$H$_{24}$Cl$_2$N$_2$O): 355. Found (MH+): 355. Anal. (calc'd for C$_{23}$H$_{28}$Cl$_2$N$_2$O$_5$.0.75H$_2$O).

EXAMPLE 12

The title compound of Example 11 1-[2-(3,4-Dichloropheyl)ethyl]-3-(1-pyrrolidinyl)-homopiperidine (0.90 g, 2.64 mmol) was reduced with AlH$_3$ in THF as described for Example 8 to give the title compound (0.85 g, 98% yield). The oxalate salt crystallized from 2-propanol: mp 161°-163° C.; $^1$H-NMR (CDCl3) ∂ 7.33 (d, J=8.2 Hz, 1H), 7.31 (d, J=2.0 Hz, 1H), 7.03 (dd, J=2.0, 8.2 Hz, 1H), 2.86 (dd, J$_{gem}$=13 Hz, J=3.9 Hz, 1H), 2.53-2.78 (complex m, 11H), 2.42 (m, 1H), 1.93 (m, 1H), 1.59-1.81 (complex m, 7H), 1.54 (m, 2H), 154 (m, 2H); CIMS (MH+ calcd for C$_{18}$H$_{26}$Cl$_2$N$_2$): 341. Found (MH+): 341; Anal. (calc'd for C$_{22}$H$_{30}$Cl$_2$N$_2$O$_8$.0.5-H$_2$O): C, H,N.

BIOLOGICAL EVALUATION

Radioreceptor Assay

The compounds of Examples 8 and 12 were tested for their ability to displace [$^3$H](+)-pentazocine from guinea pig brain membrane [de Costa et al, *FEBS Lett.*, 251, 53-58, 1989] to determine the relative potency of the compounds interacting with the sigma receptor. Receptor binding assays were performed using the crude synaptosomal (P$_2$) membrane fraction of guinea pig brain. Crude P$_2$ membrane fractions were prepared from frozen (−80° C.) guinea pig brains (Pel-Freeze, Rogers, Ark.), minus cerebella. After removal of cerebella, brains were allowed to thaw slowly on ice and placed in ice-cold 10 mM Tris-HCl, pH 7.4, containing 320 mM sucrose (Tris-sucrose buffer). Brains were then homogenized in a Potter-Elvehjem homogenizer by 10 strokes of a motor driven Teflon pestle in a volume of 10 mL/g tissue wet weight. The homogenate was centrifuged at 1000 g for 10 min at 4° C., and the supernatants were saved. The pellets were resuspended by vortexing in 2 mL/g ice-cold Tris-sucrose and centrifuged again at 1000 g for 10 min. The combined 1000 g supernatant was centrifuged at 31000 g for 15 min at 4° C. The pellets were resuspended by vortexing in 3 mL/gm of 10 mM Tris-HCl, pH 7.4, and the suspension was allowed to incubate at 25° C. for 15 min. Following centrifugation at 31000 g for 15 min, the pellets were resuspended by gentle Potter-Elvehjem homogenization to a final volume of 1.53 mL/g in 10 mM Tris-HCl, pH 7.4. Aliquots were stored at −80° C. until use. Protein concentration was determined by the method of Lowry et al. [Lowry et al, *J. Biol. Chem.*, 193, 265–271, 1951] using bovine serum albumin (BSA) as standard.

To prepare rat brain crude P$_2$ membranes, male Sprague-Dawley rats (150-200 g, Charles River, Boston, Mass.) were killed by decapitation. Brains (minus cerebella) were then treated as described above.

Each compound was initially screened at concentrations of 10, 100, and 1000 nM in order to obtain an estimate of ∂ binding affinity and to determine the appropriate concentration range to use in 12-point competition curves. For most compounds in the study, a concentration range of 0.0005-100 nM was appropriate. A range of 0.005-1000 nM or 0.05-10,000 nM was used for the less potent compounds. Twelve concentrations of unlabeled ligand were incubated with 3 nM [$^3$H](+)-pentazocine as described previously [de Costa et al, *FEBS Lett.*, 251, 53–58, 1989]. The CDATA iterative curve-fitting program (EMF Software, Inc., Baltimore, Md.) was used to determine IC$_{50}$ values. Values are the average of 2-4 experiments±SEM. Each experiment was carried out in duplicate. The Cheng-Prussoff equation [Cheng, Y. -C. and Prusoff, W. H., *Biochem. Pharacol.*, 22, 3099-3108, 1973] was then used to convert IC$_{50}$ values to apparent K$_i$ values. The K$_d$ for [3H]-(+)-pentazocine (27.4 nM) was determined in independent experiments using guinea pig brain membranes.

∂ receptors were labeled with [$^3$H]-(+)-3-pentazocine (51.7 Ci/mmol). Incubations were carried out in 50 mM Tris-HCl, pH 8.0, for 120 min at 25° C. in a volume of 0.5 mL with 500 μg of membrane protein and 3 nM [$^3$H]-(+)-pentazocine. Nonspecific binding was determined in the presence of 10 μM (+)-pentazocine. Assays were terminated by the addition of 5 mL of ice-cold 10 mM Tris-HCl, pH 8.0, and filtration through glass-fiber filters (Schleicher and Schuell). Filters were then washed twice with 5 mL of ice-cold Tris-HCl buffer. Filters were soaked in 0.5% polyethylenimine for at least 30 min at 25° C. prior to use.

TABLE II

| Test Compound | Ki([3H](+)-Pent) nM |
| --- | --- |
| DTG | 27.7 |
| Compound No. 1 | 3.56 ± 1.56 |
| Compound No. 2 | 2.67 ± 0.37 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical compositions may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological consideration such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate form the preferred dosage regimen set forth above.

For therapeutic purposes, the compounds of this invention are ordinarily combined with one or more adjuvants appropriate to the indicated route of administration. If administered the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations of parenteral administration may be in the form of aqueuos or non-aqueous isotonic sterile injection solutions of suspensions. These solutions and suspension may be prepared from sterile powders of granules having one or more of the carriers or diluents mentioned for use in the formulations for oral administration. The compounds may e dissolved in water, polyethylene glycol, propylene glycol, ethanol, corn oil, cottonseed oil, peanut oil, sesame oil, benzyl alcohol, aqueous sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

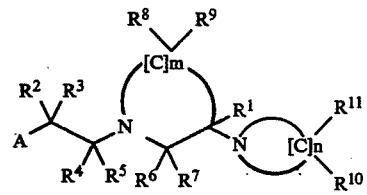

or a pharmaceutically acceptable salt thereof, wherein each of $R^1$, $R^4$, $R^5$, $R^6$ and $R^7$ is independently selected from the group consisting of methyl, ethyl, propyl, benzyl, and haloloweralkyl of one to five carbon atoms;

wherein each of $R^2$, $R^3$ and $R^8$ through $R^{11}$ is independently selected from hydrido, hydroxy, methyl, ethyl, propyl, benzyl, phenoxy, benzyloxy and haloloweralkyl of one to five carbon atoms;

wherein n is four or five and m is two or three, with the proviso that when n is four, m is three; and wherein A is phenyl, naphthyl, benzothienyl, benzofuranyl or thienyl; wherein any of the foregoing A groups can be further substituted with one or more substituents independently selected from hydroxy, methyl, ethyl, propyl, methoxy, ethoxy, methylenedioxy, halo, trifluoromethyl, amino, methylamino and dimethylamino.

2. The compound of claim 1 selected from the group consisting of
3-(1-pyrrolidinyl)-N-(2-[3,4-dichlorophenyl]ethyl)piperidine;
3-(1-piperidinyl)-N-(2-[3,4-dichlorophenyl]ethyl)piperidine;
3-(1-piperidinyl)-N-(2-[3,4-dichlorophenyl]ethyl)pyrrolidine;
3-(1-piperidinyl)-N-(2-[3-benzo[b]thienyl]ethyl)piperidine;
3-(1-pyrrolidinyl)-N-(2-[3-benzo[b]thienyl]ethyl)piperidine; and
3-(1-piperidinyl)-N-(2-[3-benzo[b]thienyl]ethyl)pyrrolidine.

3. The compound of claim 2 which is 3-(1-pyrrolidinyl)-N-(2-[3,4-dichlorophenyl]ethyl)piperidine.

4. The compound of claim 2 which is 3-(1-piperidinyl)-N-(2-[3,4-dichlorophenyl]ethyl)piperidine.

5. A pharmaceutical composition comprising a pharmaceutically-acceptable carrier or diluent and a therapeutically-effective amount of an active compound for preventing neurotoxic damage or treating or preventing cerebral ischemia, psychotic disorder or convulsive disorder, wherein said active compound is a compound of formula

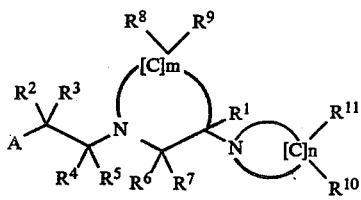

or a pharmaceutically acceptable salt thereof,
wherein each of $R^1$, $R^4$, $R^5$, $R^6$ and $R^7$ is independently selected from the group consisting of methyl, ethyl, propyl, benzyl, and haloloweralkyl of one to five carbon atoms;
wherein each of $R^2$, $R^3$ and $R^8$ through $R^{11}$ is independently selected from hydrido, hydroxy, methyl, ethyl, propyl, benzyl, phenoxy, benzyloxy and haloloweralkyl of one to five carbon atoms;
wherein n is four or five and m is two or three, with the proviso that when n is four, m is three; and
wherein A is phenyl, naphthyl, benzothienyl, benzofuranyl or thienyl; wherein any of the foregoing A groups can be further substituted with one or more substituents independently selected from hydroxy, methyl, ethyl, propyl, methoxy, ethoxy, methylenedioxy, halo, trifluoromethyl, amino, methylamino and dimethylamino.

6. The composition of claim 5 wherein the active compound is selected from the group consisting of
3-(1-pyrrolidinyl)-N-(2-[3,4-dichlorophenyl]ethyl)piperidine;
3-(1-piperidinyl)-N-(2-[3,4-dichlorophenyl]ethyl)piperidine;
3-(1-piperidinyl)-N-(2-[3,4-dichlorophenyl]ethyl)pyrrolidine;
3-(1-piperidinyl)-N-(2-[3-benzo [b]thienyl]ethyl)piperidine;
3-(1-pyrrolidinyl)-N-(2-[3-benzo[b]thienyl]ethyl)piperidine; and
3-(1-piperidinyl)-N-(2-[3-benzo[b]thienyl]ethyl)pyrrolidine.

7. The composition of claim 6 wherein the active compound is 3-(1-pyrrolidinyl)-N-(2-[3,4-dichlorophenyl]ethyl)piperidine.

8. The composition of claim 6 wherein the active compound is 3-(1-piperidinyl)-N-(2-[3,4-dichlorophenyl]ethyl)piperidine.

9. A method for treating a patient afflicted with or susceptible to neurotoxic damage, cerebral ischemia, psychotic disorder or convulsive disorder, which method comprises administering to the patient a therapeutically-effective amount of a compound of the formula

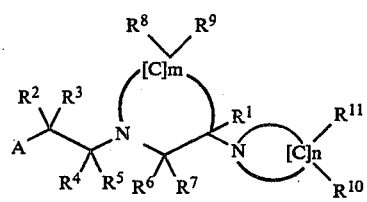

or a pharmaceutically acceptable salt thereof,
wherein each of $R^1$, $R^4$, $R^5$, $R^6$ and $R^7$ is independently selected from the group consisting of methyl, ethyl, propyl, benzyl, and haloloweralkyl of one to five carbon atoms;
wherein each of $R^2$, $R^3$ and $R^8$ through $R^{11}$ is independently selected from hydrido, hydroxy, methyl, ethyl, propyl, benzyl, phenoxy, benzyloxy and haloloweralkyl of one to five carbon atoms:
wherein n is four or five and m is two or three, with the proviso that when n is four, m is three; and
wherein A is phenyl, naphthyl, benzothienyl, benzofuranyl or thienyl; wherein any of the foregoing A groups can be further substituted with one or more substituents independently selected from hydroxy, methyl, ethyl, propyl, methoxy, ethoxy, methylenedioxy, halo, trifluoromethyl, amino, methylamino and dimethylamino.

10. The method of claim 9 wherein the compound is selected from the group consisting of
3-(1-pyrrolidinyl)-N-(2-[3,4-dichlorophenyl]ethyl)piperidine;
3-(1-piperidinyl)-N-(2-[3,4-dichlorophenyl]ethyl)piperidine;
3-(1-piperidinyl)-N-(2-[3,4-dichlorophenyl]ethyl)pyrrolidine;
3-(1-piperidinyl)-N-(2-[3-benzo [b]thienyl]ethyl)piperidine;
3-(1-pyrrolidinyl)-N-(2-[3-benzo [b]thienyl]ethyl)piperidine; and
3-(1-piperidinyl)-N-(2-[3-benzo[b]thienyl]ethyl)pyrrolidine.

11. The method of claim 10 wherein the compound is 3-(1-pyrrolidinyl)-N-(2-[3,4-dichlorophenyl]ethyl)piperidine.

12. The method of claim 10 wherein the compound is 3-(1-piperidinyl)-N-(2-[3,4-dichlorophenyl]ethyl)piperidine.

* * * * *